United States Patent [19]
Chaplin et al.

[11] Patent Number: 6,093,815
[45] Date of Patent: Jul. 25, 2000

[54] GALANTHAMINE DERIVATIVES AND PROCESS FOR THEIR PREPARATION

[75] Inventors: David Andrew Chaplin; Neil Fraser; Peter David Tiffin, all of Cambridge, United Kingdom

[73] Assignee: Janssen Pharmaceutica N.V., Belgium

[21] Appl. No.: 09/043,330

[22] PCT Filed: Sep. 23, 1996

[86] PCT No.: PCT/GB96/02334

§ 371 Date: Aug. 20, 1998

§ 102(e) Date: Aug. 20, 1998

[87] PCT Pub. No.: WO97/11077

PCT Pub. Date: Mar. 27, 1997

[30] Foreign Application Priority Data

Sep. 21, 1995 [GB] United Kingdom ............... 9519267

[51] Int. Cl.[7] .................................................. A61K 31/55
[52] U.S. Cl. ............................................................ 540/581
[58] Field of Search ............................................. 540/581

[56] References Cited

FOREIGN PATENT DOCUMENTS 401058 of 0000 Austria.
WO 88/08708 11/1988 WIPO.

OTHER PUBLICATIONS

Shimzu et al. (Heterocycles (1977), 8, 277–82), 1977.
Heinsch et al. (Monatsch. Chem., 102 (1971), 530–537), 1971.
Shimizu, K. et al. (1978) Stereochemical Studies. LIV. A Biogenetic–type Asymmetric Synthesis of optically Active Galanthamine from L–Tyrosine. Chem. Pharm. Bull. 26(12): 3765–3771.
Szewczyk, J. Lewin, A.H., Carroll, F.I. (1988) An Improved Synthesis of Galanthamine. J. Heterocyclic Chem. 25: 1809–1811.
Kametani, T. et al. (1969) Studies on the Syntheses of Heterocyclic Compounds. Part CCCXV. Modified Total Synthesis of (+/−)—Galanthamine through Phenol Oxidation. J. Chem. Soc. (C): 2602–2605.
Vlahov, R. et al. (1989) Synthesis of Galanthamine and Related Alkaloids. Tetrahedron 45(11): 3329–3345.

*Primary Examiner*—Mukund J. Shah
*Assistant Examiner*—Bruck Kifle
*Attorney, Agent, or Firm*—Saliwanchik, Lloyd & Saliwanchik

[57] ABSTRACT

A process for preparing a compound having formula (11), comprises oxidative cyclization of a tertiary amine having formula (12), wherein $X^1$ is a removable functionality, $X^2$ is hydrogen or a group as defined above for $X^1$, and $R^1$ is selected from hydrogen and alkyl, aryl, alkaryl and aralkyl groups having up to 20 carbon atoms, and $R^2$ and $R^3$ are independently selected from hydrogen and alkyl, aryl, alkaryl, aralkyl and acyl groups having up to 20 carbon atoms. Novel compounds are both used and produced by that process.

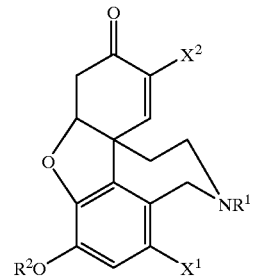

(11)

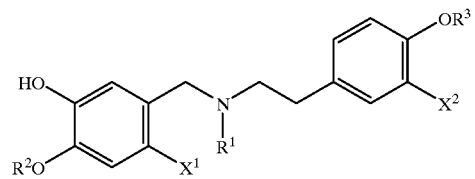

(12)

16 Claims, No Drawings

GALANTHAMINE DERIVATIVES AND PROCESS FOR THEIR PREPARATION

FIELD OF THE INVENTION

This invention relates to the discovery of a novel process for the manufacture of galanthamine and related compounds, in racemic or in optically-enriched form, and to novel intermediates in that process.

BACKGROUND OF THE INVENTION (−)-Galanthamine (and related compounds) are useful compounds for the treatment of Alzheimer's disease and related illnesses. Currently galanthamine is usually obtained by extraction from particular types of bulbs, such as daffodils or snowdrops.

It is known that single enantiomer galanthamine (2) can be prepared from racemic narwedine (1) through resolution followed by reduction of the enone function, as depicted in Scheme 1, below. Usefully, since the enantiomers of narwedine (1) readily equilibrate (racemise) by way of reversible ring opening to a dienone, coupled to the fact that crystals of racemic (1) exist as a conglomerate of enantiomers, a dynamic resolution of (1) can be carried out by crystallisation with entrainment by crystals of the desired isomer (see Barton and Kirby, J. Chem. Soc. (C) (1962) 806). However, in respect of a total synthesis, racemic narwedine itself is not readily available.

Numerous processes have been based on the biomimetic approach pioneered by Barton and Kirby in 1962, in which the key oxidative cyclisation step proceeded in only 1.4% yield. In later studies it was found that the yields of the phenolic coupling could be increased substantially by deactivation of the basic amine as either an amide or sulphonamide group, and by blocking the para-position with a removable group (i.e. replaceable by hydrogen) such as bromine, e.g. as in compound (3) in Scheme 2 below; see for instance Franck and Lubs, Liebigs. Ann. Chem. (1968) 720: 131; Kametani et al., J. Chem. Soc., Chem. Comm. (1969) 425 and J. Chem. Soc.(C) (1969) 2602–2605 and Szewczyk et al., J. Heterocyclic Chem. (1988) 1809).

However, processes operating on this strategy are cumbersome owing to the need to remove the amine protecting group from the product of the phenolic coupling (compound (4) in Scheme 2) by reduction. This invariably leads to concomitant reduction of the narwedine carbonyl group, and possibly other functional groups, producing racemic galanthamine and/or epigalanthamine, or derivatives thereof, as depicted by compound (5) in Scheme 2. To obtain racemic narwedine (1) from the latter compounds then requires a separate reoxidation step.

SUMMARY OF THE INVENTION

Surprisingly, it has now been discovered that phenolic coupling of the general type described above can be carried out with acceptable yield without the need to render nonbasic the amine functionality in the cyclisation precursor. This discovery is particularly advantageous because the product of the phenolic coupling does not need to undergo the cumbersome reduction-oxidation procedure to afford narwedine.

Accordingly, in one aspect of the present invention a process for preparing an optically-enriched compound having the formula (11), below, comprises oxidative cyclisation of a tertiary amine having the formula (12), below, wherein $X^1$ is a removable functionality, $X^2$ is hydrogen or a removable functionality, $R^1$ is selected from hydrogen and alkyl, aryl, alkaryl, aralkyl groups having up to 20 carbon atoms, and $R^2$ and $R^3$ are independently selected from hydrogen and alkyl, aryl, alkaryl, aralkyl and acyl groups having up to 20 carbon atoms. Resolution and reduction of the resulting compounds leads to optically-enriched compounds having the galanthamine structure as depicted by formula (10), below.

According to other aspects of the present invention, novel compounds having the formulae (10), (11) and (12) and are defined in the claims. Of particular interest are the optically-enriched forms of compounds (10) and (11), and in particular when enriched in the enantiomer which has the stereochemical configuration of (−)-galanthamine, which therefore allow ready access to (−)-galanthamine per se. By optically-enriched typically we mean an enantiomeric excess of at least 50%, preferably at least 80%, more preferably at least 90% or higher, thereby including single enantiomer form.

DESCRIPTION OF THE INVENTION

In the above, $X^1$ is described as a removable functionality, which means any group replaceable by hydrogen. Examples of suitable groups for $X^1$ include the halogens, tert-butyl and O-E groups, wherein E comprises a group linked by a carbon, sulphur or phosphorus atom. Preferably $X^1$ is a halogen atom, and more preferably it is bromine.

As has been explained above, the key to the present invention is that $R^1$ need not be acyl, or some other protecting group for the nitrogen atom, to achieve acceptable yield in the phenolic coupling reaction. Preferably $R^1$ is alkyl, preferably $C_{1-10}$ alkyl, and most preferably methyl. For instance, a preferred cyclisation is shown in Scheme 3 below, where the amine (6) is converted to bromonarwedine (7). This can then be readily reduced, or de-brominated, to racemic narwedine by an appropriate chemoselective method, eg. using a palladium catalyst, which can then be resolved, for instance as described by Shieh et al, J. Org. Chem. (1994) 59: 5463, for subsequent conversion to the corresponding galanthamine structure. Alternatively, racemic bromonarwedine, or a salt derivative thereof, can be converted by dynamic entrainment or crystallisation into an optically-enriched form thereof, for example using a method of the general type described by Barton et al or by Shieh et al, discussed above. This can then be converted into optically-enriched bromogalanthamine, for instance (−)-bromogalanthamine of formula (8), below, by reduction, for instance as described in International Application No. PCT/GB96/00843. The bromine atom can then be removed as described above, or replaced by different functionality.

Bromination of O'-dimethylgalanthamine has recently been described in EP-A-0649846 and EP-A-0648771, and this procedure affords the regioisomeric bromine derivative (9) which can be converted into galanthamine analogues. The availability of bromonarwedine and bromogalanthamine by virtue of the present invention, therefore, provides a possible entry into other galanthamine analogues which would not be accessible via semi-synthetic routes from galanthamine obtained from natural sources.

The tertiary amine substrate for the phenolic coupling reaction can be made by any of the known techniques. For instance, it can be made by reductive amination from 6-bromoisovanillin (from either isovanillin or veratraldehyde) and tyramine (or N-methyltyramine). Reference is made in this respect to Kametani et al and Szewczyk et al, mentioned above, and to Bulavka et al, Khim. Farm. ZH. (1990) 24: 59.

While the above description concentrates on the (−)-enantiomers of the respective compounds, as these allow ready access to the therapeutically-useful (−)-galanthamine, the chemistry is equally applicable to the (+)-enantiomers.

The present invention is now further illustrated by the following Examples.

EXAMPLES

Example 1

N,p-O'-Dimethylbromonorbelladine (6)

6-Bromoisovanillin (500 g) was suspended in MeOH (2.5 l) in a 5 l 3-necked flask equipped with an overhead stirrer. Tyramine was added and the resulting mixture was stirred at room temperature for 60 min and then cooled to 0° C. NaBH$_4$ (67 g) was then added in approx 2.5 g portions keeping the temperature below 20° C., eventually forming a solution. After stirring for a further 60 min a precipitate had formed. HCHO (37% aq solution) (179 ml) was added in one portion at room temperature and stirred for 60 min during which time a solution formed. The solution was cooled to 0° C. and NaBH$_4$ (31.0 g) added, again in approx 2.5 g portions keeping the temperature below 20° C. The mixture then became quite thick as a white solid formed. MeOH (2.5 l) was added to mobilise the mixture, which was then filtered to collect the white solid, washing with cold MeOH. Yield=780 g, 98%.

The N,p-O'-Dimethyl-6-bromonorbelladine (6) obtained (300 g) was dissolved in IMS (3.0 l) and treated with charcoal (10 g). After hot filtration the solution was allowed to cool yielding a white crystalline solid. Recovery=231 g, 77%.

Example 2

Racemic Bromonarwedine (7)

Toluene (2.67 l) and water (333 ml) were placed in a 5 l jacketed vessel and the mixture was heated to 70° C. under nitrogen. K$_2$CO$_3$ (33 g, 0.24 mol) and K$_3$Fe(CN)$_6$ were added and then the homogenizer was turned on. N,p-O'-Dimethyl-6-bromonorbelladine (6) (20 g, 52.6 mmol) was then added in one portion. After 30 min. the homogenizer was turned off and the mixture was filtered to remove a large amount of brown solid. The two layers were separated and the toluene phase was washed with NaOH (2 M; 500 ml). The product was then extracted into HCl (2 M, 500 ml). TBME (500 ml) and EtOAc (250 ml) were added and the aqueous layer was neutralised. The organic phase was dried over Na$_2$SO$_4$ and concentrated in vacuo to yield bromonarwedine (7) (6.27 g, 33%).

Example 3

Racemic Bromonarwedine (7)

N,p-O'-Dimethylbromonorbelladine (6) (as its formate salt) (1 g) was added to a stirred mixture of potassium ferricyanide (5.39 g) in 5% aqueous sodium hydrogen carbonate (50 ml) and toluene (100 ml) and the mixture heated at 85° C. for 3 hours. The mixture was cooled and filtered. The layers were separated and the organic phase evaporated to give racemic bromonarwedine (7) (0.113 g, 13%) substantially pure by NMR analysis.

Example 4

Racemic Narwedine (1)

DMF (930 ml) was added to bromonarwedine (7) (187.3 g, 515 mmol), NaCO$_2$H (52.5 g, 772 mmol), PPh$_3$ (13.5 g, 51 mmol), Pd(OAc)$_2$ (5.78 g, 26 mmol) and NaCl (3.76 g, 103 mmol). The mixture was heated to 94° C., for 6 hours at which point GC indicated complete reaction. The dark mixture was diluted with CH$_2$Cl$_2$ (2 l) and filtered. 2 M NaOH (2 l) was added and the layers separated. The product was extracted from the CH$_2$Cl$_2$ using 2 M HCl (2 l). This was added to CH$_2$Cl$_2$ (2 l) and the pH adjusted to 12 using 46–48% NaOH. The CH$_2$Cl$_2$ was separated and concentrated to approx 200 ml. MeOH (100 ml) was added and the remainder of the CH$_2$Cl$_2$ evaporated. The solid product formed (1) was collected by filtration washing with cold MeOH. Yield=122.2 g, 84%, purity>95% by HPLC.

The racemic narwedine obtained in Example 4 can then be converted to optically-enriched galanthamine as described above.

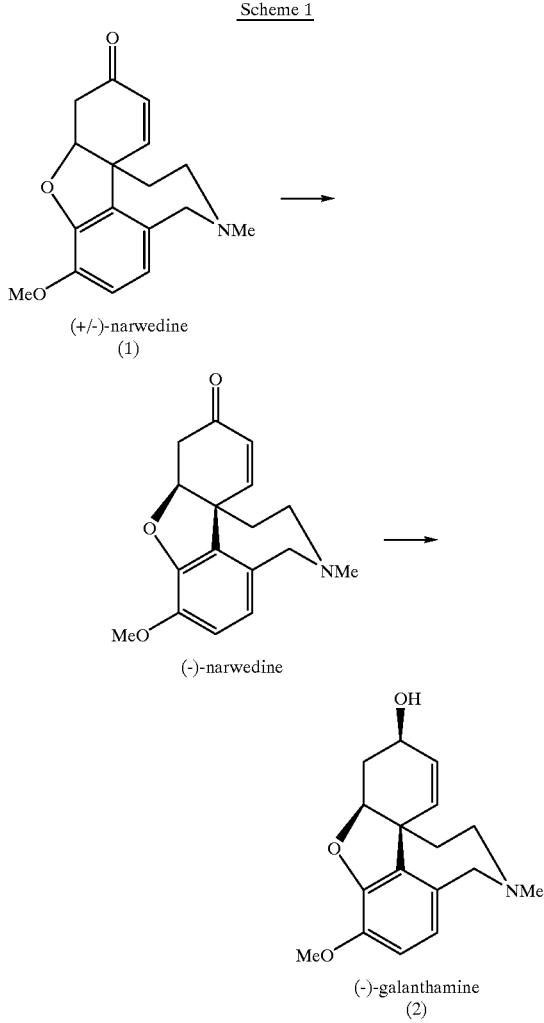

Scheme 1

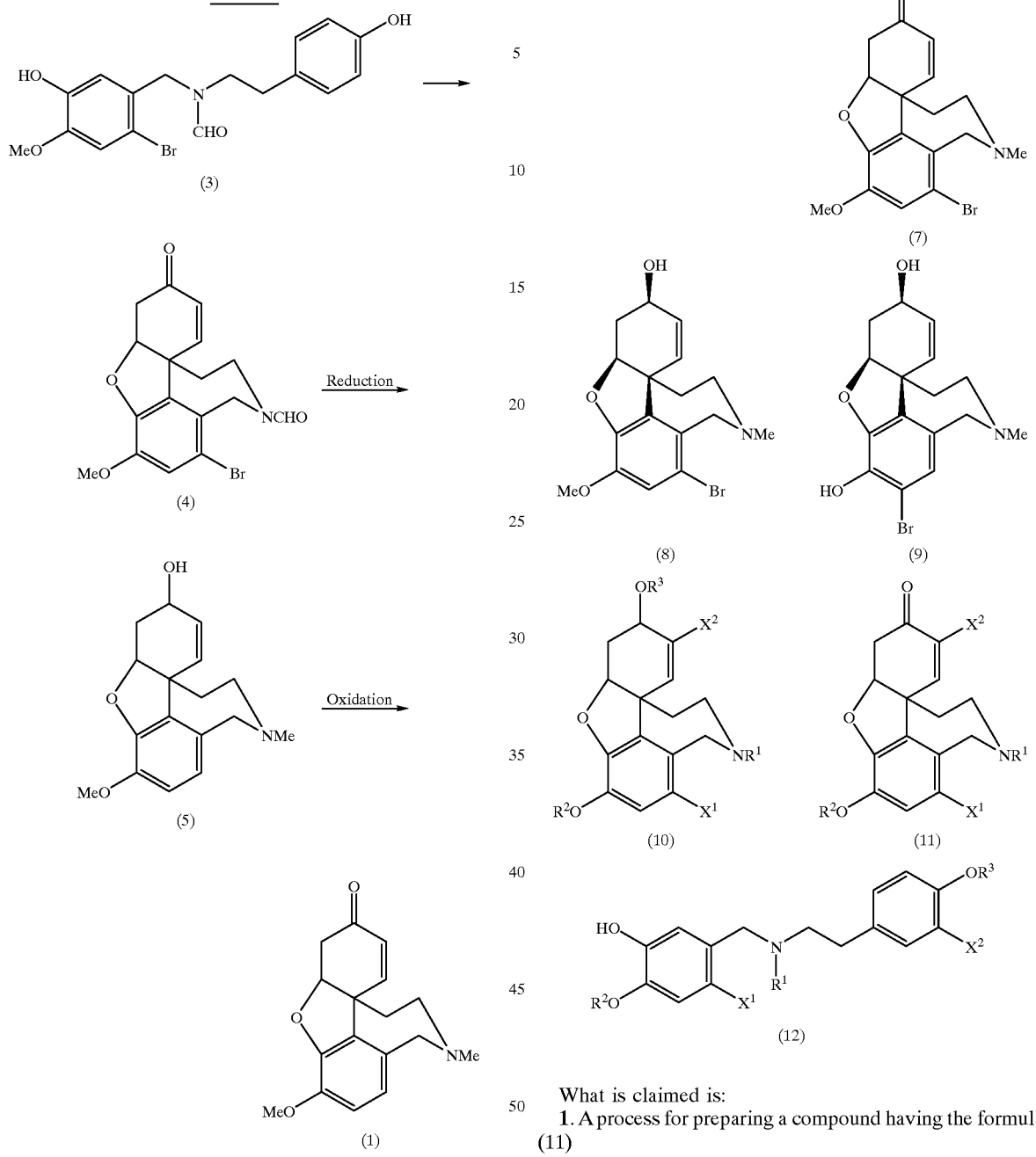
What is claimed is:
1. A process for preparing a compound having the formula (11)
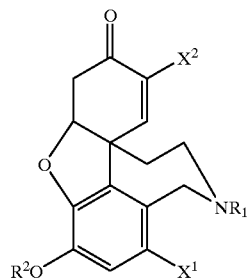

comprising oxidative cyclisation of a tertiary amine having the formula (12)

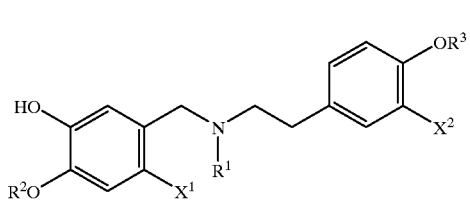
(12)

wherein $X^1$ is a halogen or t-butyl, $X^2$ is hydrogen or a group as defined above for $X^1$, and $R^1$ is selected from hydrogen and alkyl, aryl, alkaryl and aralkyl groups having up to 20 carbon atoms, and $R^2$ and $R^3$ are independently selected from hydrogen and alkyl, aryl, alkaryl, aralkyl and acyl groups having up to 20 carbon atoms.

2. The process according to claim 1, wherein $R^1=R^2=$ methyl, $R^3=$hydrogen, $X^1=$bromine and $X^2=$hydrogen.

3. The process according to claim 1 or claim 2, which further comprises resolving the compound (11) to give compound (11) in optically-enriched form.

4. A process for preparing an optically-enriched compound having the formula (10),

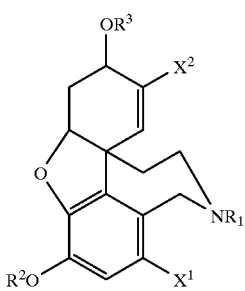
(10)

in which the R and X groups are as defined in claim 1, comprising a process as defined in claim 3, followed by reduction of the product thereof.

5. A process for preparing an optically-enriched compound having the formula (10),

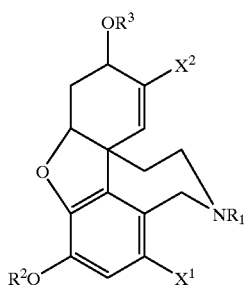
(10)

in which the R and X groups are as defined in claim 1, comprising a process as defined in claim 1, followed by reduction of the product thereof to give a racemic compound of formula (10), and subsequent resolution thereof.

6. A process for preparing an optically-enriched compound of formula (10)

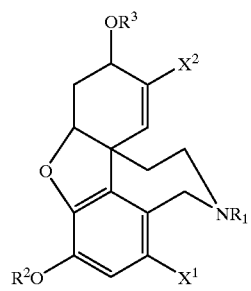
(10)

in which the R groups and $X^2$ are as defined in claim 1, and $X^1=$hydrogen, comprising preparing an optically-enriched precursor compound of formula (10) by a process as defined in claim 4, and removing therefrom the $X^1$ substituent.

7. The process according to claim 3, for preparing optically-enriched galanthamine, wherein in the precursor compound $R^1=R^2=$methyl, $X^1=$bromine and $X^2=$hydrogen.

8. A process for preparing an optically-enriched compound of formula (10)

(10)

in which the R groups and $X^2$ are as defined in claim 1 and $X^1=$hydrogen, comprising preparing a compound of formula (11) as defined in claim 1, removing therefrom the $X^1$ substituent, and reducing and resolving the product obtained as defined in claim 4.

9. The process according to claim 2, wherein the compound (11) is resolved by entrainment or crystallisation of a salt thereof.

10. The process according to claim 1, wherein $R^1$ is selected from the group consisting of hydrogen and alkyl, aryl and alkaryl groups having up to 20 carbon atoms.

11. The process according to claim 1, wherein $R^1$ is selected from the group consisting of alkyl, aryl and alkaryl groups having up to 20 carbon atoms.

12. A process for preparing a compound of formula (11)

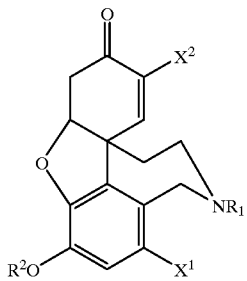
(11)

in which the R groups and $X^2$ are as defined in claim 1 and $X^1$ is hydrogen, comprising reductive debromination of a precursor compound of formula (11) in which R and $X^2$ are as defined in claim 1 and $X^1$ is bromine, to convert $X^1$ from bromine to hydrogen.

13. The process according to claim 12, wherein in the precursor compound both $R^1$ and $R^2$ are methyl and $X^2$ is hydrogen.

14. The process according to claim 12, which further comprises resolving the product obtained to form an optically-enriched form of compound (11).

15. The process according to claim 13, which further comprises resolving the product obtained to form an optically-enriched form of compound (11).

16. The process according to claim 12, wherein the precursor compound of formula (11) is prepared by a process as defined in claim 1.

* * * * *

UNITED STATES PATENT AND TRADEMARK OFFICE
CERTIFICATE OF CORRECTION

PATENT NO. : 6,093,815
DATED : July 25, 2000
INVENTOR(S) : David Andrew Chaplin, Neil Fraser, Peter David Tiffin It is certified that error appears in the above-identified patent and that said Letters Patent is hereby corrected as shown below:

Column 8,
Line 23, "claim 3" should read -- claim 6 --.
Line 54, "claim 2" should read -- claim 3 --.

Signed and Sealed this

Sixth Day of November, 2001

Attest:

*Nicholas P. Godici*

NICHOLAS P. GODICI
*Attesting Officer*    *Acting Director of the United States Patent and Trademark Office*